US00PP36648P2

(12) United States Plant Patent
Zlesak

(10) Patent No.: US PP36,648 P2
(45) Date of Patent: May 6, 2025

(54) ***CORNUS* PLANT NAMED 'Zelroc3423'**

(50) Latin Name: *Cornus sericea*
Varietal Denomination: Zelroc3423

(71) Applicant: The Conard Pyle Company, West Grove, PA (US)

(72) Inventor: David Charles Zlesak, River Falls, WI (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/931,397

(22) Filed: Oct. 30, 2024

(51) Int. Cl.
*A01H 5/00* (2018.01)
*A01H 6/00* (2018.01)

(52) U.S. Cl.
USPC ..... Plt./220

(58) Field of Classification Search
USPC ..... Plt./216, 220
See application file for complete search history.

(56) References Cited

U.S. PATENT DOCUMENTS

PP18,523 P2 2/2008 Farrow
PP27,402 P2 * 11/2016 Ronald ..... A01H 6/00 Plt./220

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of *Cornus* plant, referred to by its cultivar name, 'Zelroc3423', is described. The new variety forms creamy, white colored flowers. The growth habit is compact. Green colored foliage is formed. Bright, red colored stems are exhibited in winter. Additionally, the new variety is particularly well suited for growing as distinctive ornamentation in the landscape.

3 Drawing Sheets

Figure 1:
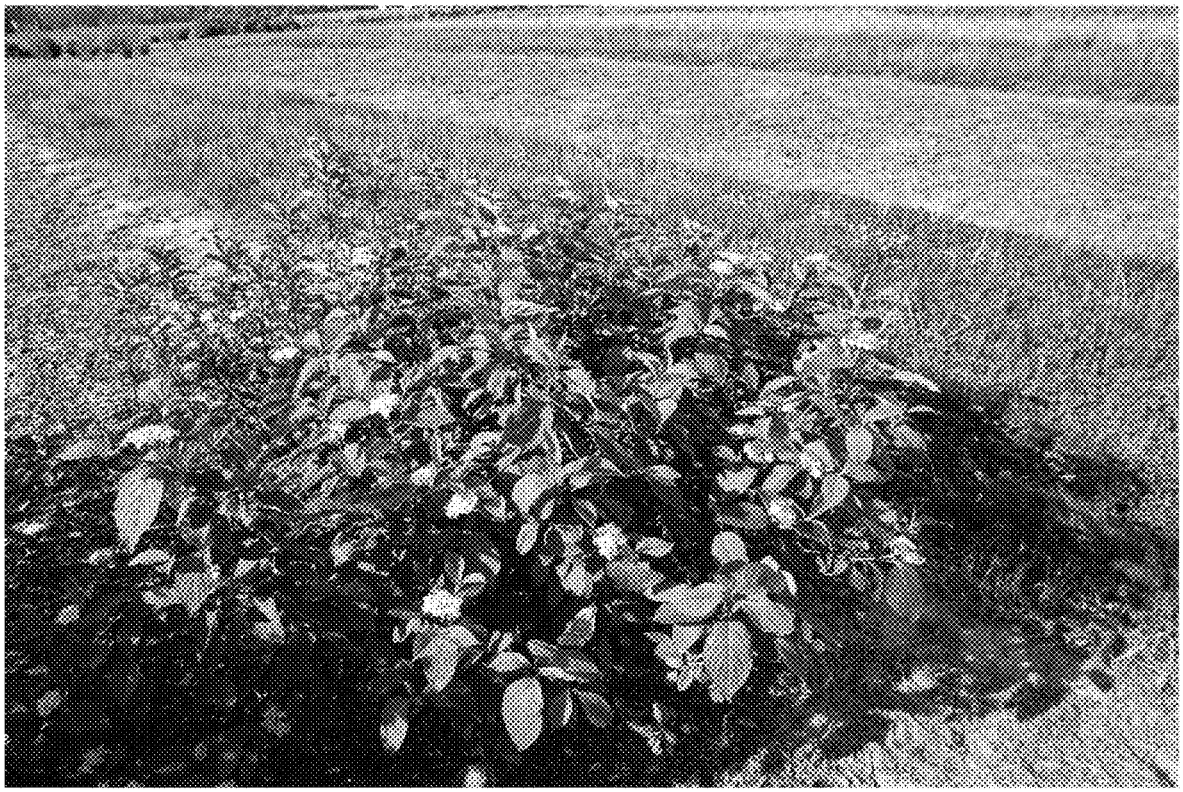

Latin name of genus and species of plant claimed: *Cornus sericea.*

Variety denomination: 'Zelroc3423'.

STATEMENT REGARDING PRIOR DISCLOSURES BY THE INVENTOR

The first sale or offer for sale of the new variety was on Dec. 14, 2023, to Greenleaf Nursery in the United States of America. The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Cornus* plant of the present invention was created by open pollination at River Falls, Wisconsin. The female parent (i.e., the seed parent) of the new variety is unknown and the male parent (i.e., the pollen parent) of the new variety is unknown. The collection of genotypes in the open pollination population included plants with yellow stems and stems that were different shades of red. The seeds resulting from the open pollination were sown and small plants were obtained that were physically and biologically different from each other. The new variety was discovered and selected as a single seedling resulting from the above-described open pollination in a controlled environment in River Falls, Wisconsin.

The new variety has been found to undergo asexual propagation in River Falls, Wisonsin by a number of routes such as softwood, semi-hardwood, and hardwood cuttings. Asexual propagation techniques in River Falls, Wisonsin have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of *Cornus* plant of the present invention possesses the following combination of characteristics:

(a) forms creamy, white colored flowers,
(b) provides green colored foliage,
(c) exhibits a compact growth habit, and
(d) provides bright, red colored stems in winter.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. Although the parent varieties are unknown, all the plants that seed were harvested from in the open pollination that created the new variety, had a larger overall mature plant size compared to plants of the new variety. The new variety can be readily distinguished from similar varieties. For example, of the many commercially available *Cornus* cultivars, the most similar in comparison to the new cultivar is the 'Farrow' variety (U.S. Plant Pat. No. 18,523). The new variety displays a more compact growth habit compared to the 'Farrow' variety, and the 'Farrow' variety exhibits a darker green colored upper surface foliage compared to the new variety.

The new variety has been named the 'Zelroc3423' variety.

BRIEF DESCRIPTION OF THE PHOTOGRAPHS

The accompanying photographs show, as nearly true as it is reasonably possible to make the same in a color illustration of this character typical flower, foliage, and stem color characteristics of the new cultivar. Colors in the photographs may differ slightly from the color values cited in the detailed description, which accurately describes the colors of 'Zelroc3423'. The illustrated plants of the new variety were approximately three years of age and were grown outdoors in Cochranville, Pennsylvania.

FIG. 1—illustrates a specimen of the plant displaying the overall growth and flowering habit-side view, photograph taken May 2024.

Figure 2:
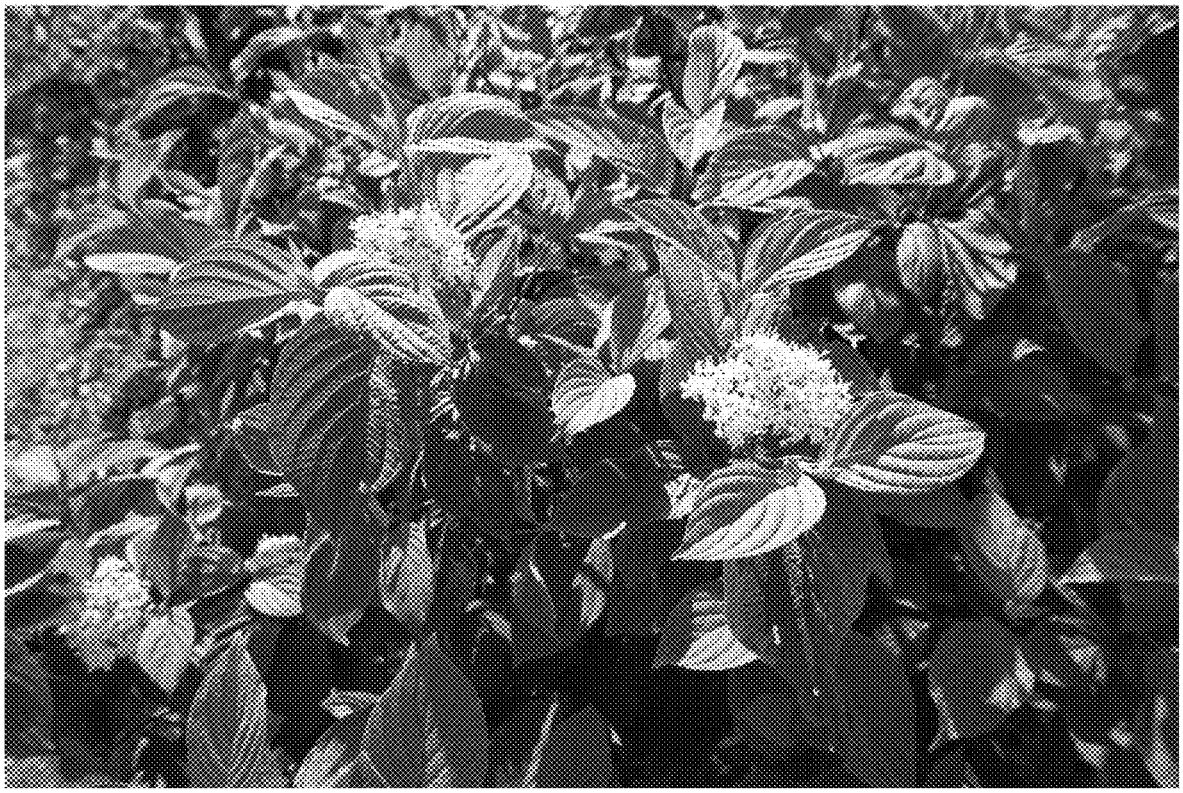

FIG. 2—illustrates a close-up view of an inflorescence of the new variety, photograph taken May 2024.

Figure 3:
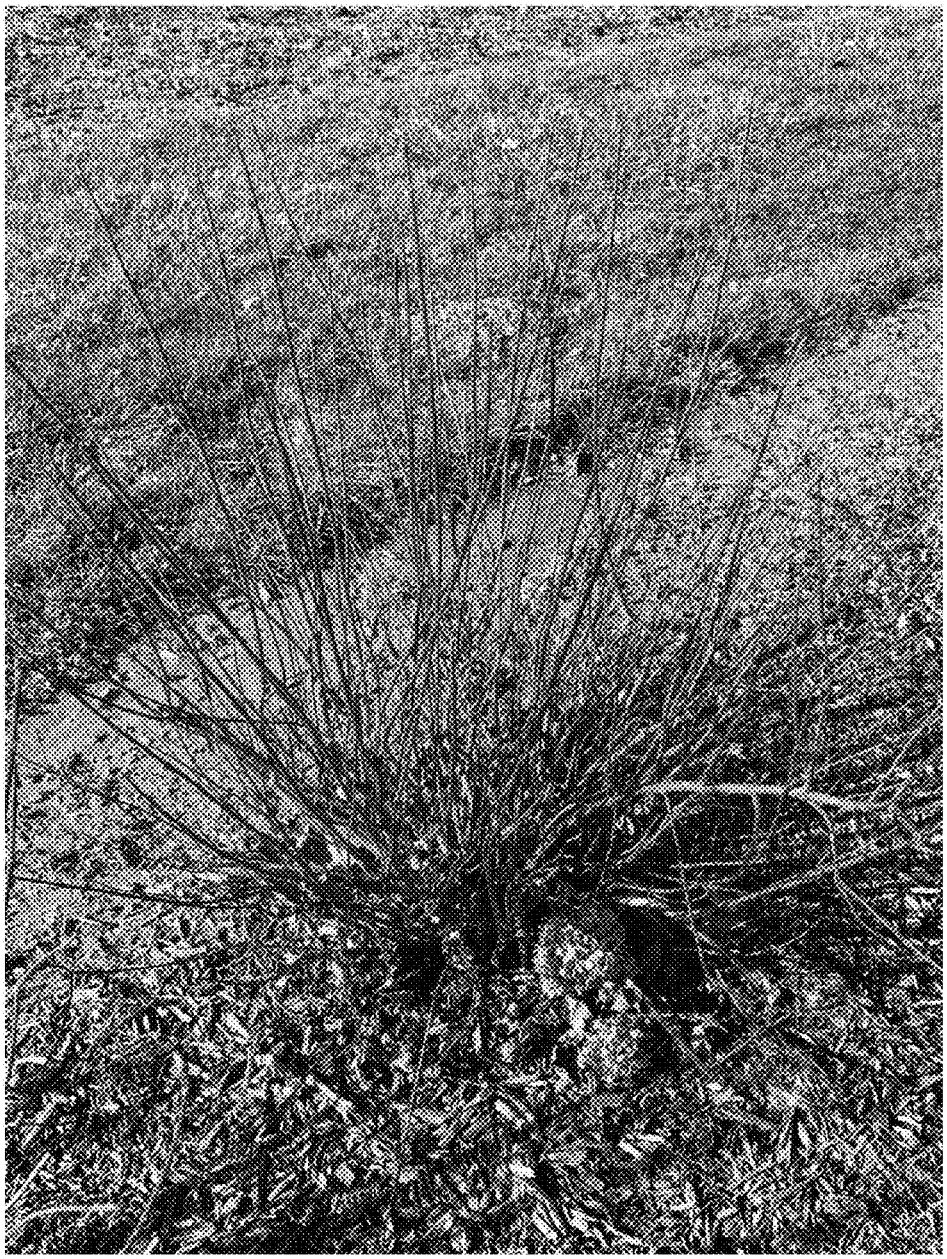

FIG. 3—illustrates a close-up view of the winter stem color of the new variety, photograph taken January 2024.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on 24 months old plants produced from cuttings from stock plants and growing outdoors in 3-gallon containers in Cochranville, Pennsylvania and observed during May 2024, under natural light conditions. Measurements and numerical values represent averages of typical plants.

Botanical classification: *Cornus sericea* cultivar 'Zelroc3423'.

Propagation:

*Type cutting*.—Softwood.

*Time to initiate roots*.—Approximately 21 to 28 days.

*Time to produce a rooted cutting*.—Approximately 60 to 70 days.

*Root description*.—Fine to thick; white to brown in color.

*Rooting habit*.—Freely branching; dense.

Plant:

*Habit*.—Multi-stemmed, deciduous shrub, moderately vigorous, compact habit.

*Commercial crop time*.—Approximately 26 to 30 weeks from a rooted cutting to finish in a 1-gallon container.

*Size*.—Approximately 50.0 cm in height from soil level to top of plant plane; and approximately 60.0 cm in width.

Branches:

*Branching habit*.—Freely branching, pinching enhances branching.

*Quantity of lateral branches per plant*.—Approximately 10.

*Strength*.—Strong.

*Shape*.—Rounded.

*Arrangement*.—Opposite.

*Aspect*.—Erect to about 45° from main stem.

*Size*.—Length of base to inflorescence: approximately 18.01 cm. — diameter: approximately 3.0 mm. — length of central internode: approximately 6.0 cm.

*Texture*.—Young stems: glabrous to slightly pubescent. — mature stems: woody.

*Color*.—Young stems: Green Group 143C. — mature stems: Greyed-Orange Group 174A. — winter color of mature stems: Greyed-Purple Group 187C.

Foliage:

*Fragrance*.—None detected.

*Form*.—Simple.

*Arrangement*.—Opposite.

Leaves:

*Shape*.—General: lanceolate. — margin: entire. — apex: acuminate. — base: rounded.

*Venation*.—Pattern: pinnate.

*Size*.—Length of mature leaf: approximately 12.0 cm. — width of mature leaf: approximately 7.0 cm.

*Texture*.—Upper and lower surfaces: glabrous to tomentulose.

*Color*.—Upper surface of young and mature foliage: Green Group 143A with venation of Yellow-Green Group 144B. — lower surface of young and mature foliage: Green Group 138B with venation of Green Group 139D.

*Petiole*.—Length: approximately 2.5 cm. — diameter: approximately 2.0 mm. — texture: Glabrous to tomentulose. — color: Orange-White Group 159A.

Flower:

*Type*.—Compound corymbs; flowering on current season's growth, terminal and often on subtending axils; sepals arranged in a whorl.

*Quantity*.—Approximately 20 inflorescences open at a given time per plant; and approximately 140-200 flowers per inflorescence.

*Fragrance*.—Very light.

*Aspect*.—Erect.

*Inflorescence diameter*.—Approximately 3.0 to 5.0 cm.

*Flower diameter*.—Approximately 9.0 mm.

*Flower depth*.—Approximately 0.8 mm.

*Bud just before opening*.—Shape: ovate. — length: approximately 4.0 mm. — diameter: approximately 2.0 mm. — color of petals: Yellow-Green Group 144B.

*Petals*.—Quantity: approximately 4. — shape: linear. margin: entire. apex: acute. base: truncate. — length: approximately 5.0 mm. — width: approximately 1.8 mm. — texture of upper and lower surfaces: glabrous. — color of upper and lower surfaces: White Group NN155A.

*Peduncle*.—Strength: strong. — aspect: erect. — length: approximately 8.0 mm. — width: approximately 1.0 mm. — texture: tomentulose. — color: Yellow-Green Group 145A.

*Reproductive organs*.—Androecium: stamen: quantity per flower is 4; length is approximately 3.0 mm to 4.0 mm. filament: sessile. anther: shape is oblong; length is approximately 1.3 mm; and color is Yellow-White Group 158A. pollen: amount is moderate;

color is Yellow Group 4C. — gynoecium: pistil: approximately 1 per flower; length is approximately 4.0 mm. stigma: shape is rounded; length is approximately 2.5 mm; color is Yellow-Green Group 145D. style: length is approximately 2.5 mm; color is Yellow-Green Group 144D. ovary: length is approximately 1.0 mm on average; color is Green Group 142B. — fruit: diameter is approximately 5.0 mm; width is approximately 5.0 mm; texture is glabrous; flesh color is White Group 155B. — seed: not observed to date.

Development:

*Flowering season*.—Flowers in mid-spring with sporadic blooming through summer.

*Lastingness of individual flower*.—Approximately 10 to 15 days.

*Hardiness*.—USDA Zones 3-8.

*Tolerance to disease and pest*.—Not observed to date.

The new 'Zelroc3423' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Cornus* plant named 'Zelroc3423' characterized by the following combination of characteristics:

(a) forms creamy, white colored flowers, (b) provides green colored foliage, (c) exhibits a compact growth habit, and (d) provides bright, red colored stems in winter, substantially as herein shown and described.

* * * * *